United States Patent
Luizzi et al.

(10) Patent No.: US 6,447,495 B1
(45) Date of Patent: Sep. 10, 2002

(54) WINGED ABSORBENT ARTICLE WITH COHESIVELY BONDED BRIDGING UNIT

(75) Inventors: Joseph Luizzi, Newtown, PA (US); Melinda Cettina, Robbinsville, NJ (US)

(73) Assignee: McNeill-PPC, Inc., Skillman, NJ (US)

( * ) Notice: Subject to any disclaimer, the term of this patent is extended or adjusted under 35 U.S.C. 154(b) by 0 days.

(21) Appl. No.: 09/520,496

(22) Filed: Mar. 8, 2000

(51) Int. Cl.[7] .................................................. A61F 13/15
(52) U.S. Cl. ........................... 604/385.05; 604/385.03; 604/385.04; 604/386; 604/387; 604/389; 604/390
(58) Field of Search ................... 604/385.03, 385.04, 604/385.05, 385.01, 386, 387, 389, 390

(56) References Cited

U.S. PATENT DOCUMENTS

| | | |
|---|---|---|
| 4,285,343 A | 8/1981 | McNair |
| 4,589,876 A | 5/1986 | Van Tilburg |
| 4,608,047 A | 8/1986 | Mattingly |
| 4,687,478 A | 8/1987 | Van Tilburg |
| 4,701,178 A | 10/1987 | Glaug et al. |
| 4,759,754 A | 7/1988 | Korpman |
| 5,133,704 A * | 7/1992 | Wheeler ........................ 604/387 |
| 5,562,651 A * | 10/1996 | Ahr ................................ 604/387 |
| 5,620,430 A * | 4/1997 | Bamber ...................... 604/385.2 |
| 5,662,639 A * | 9/1997 | Tanaka et al. ................ 604/387 |
| 5,800,654 A * | 9/1998 | Davis et al. .................. 156/227 |
| 5,868,727 A * | 2/1999 | Barr et al. .................... 604/387 |
| 5,873,871 A * | 2/1999 | Lavash et al. ................ 604/386 |
| 6,074,376 A * | 6/2000 | Mills ............................. 604/390 |
| 6,168,582 B1 * | 1/2001 | Hasegawa ................ 604/385.02 |

FOREIGN PATENT DOCUMENTS

| | | | |
|---|---|---|---|
| EP | 0 347 319 B1 | 1/1993 | ........... A61F/13/15 |
| WO | WO 88/04546 | 6/1988 | ........... A61F/13/16 |

* cited by examiner

Primary Examiner—John G. Weiss
Assistant Examiner—Jacqueline F Stephens
(74) Attorney, Agent, or Firm—James P. Barr

(57) ABSTRACT

The present invention is directed to a sanitary napkin having flaps folded onto the topsheet of the napkin and held in this position by a unitary bridging strip. Each of these flaps has an adhesive area that is used to attach the flap to the undergarment. A release strip covers each such adhesive area. These release strips and the bridging strip each contain a cohesive layer whereby a cohesive bond is formed between the bridging strip and each release strip thereby holding the flaps in their folded position.

24 Claims, 6 Drawing Sheets

WINGED ABSORBENT ARTICLE WITH COHESIVELY BONDED BRIDGING UNIT

FIELD OF THE INVENTION

This invention is directed to sanitary napkins, and particularly to sanitary napkins having flaps. More particularly, this invention is directed to an efficient method of securing these flaps that enhances convenience in both manufacturing and in use to the wearer.

BACKGROUND OF THE INVENTION

Sanitary napkins having flaps extending outwardly from the longitudinal side margins are well known in the art. For example, U.S. Pat. No. 4,589,876 issued May 20, 1986, to Van Tilburg and U.S. Pat No. 4,687,478 issued Aug. 18, 1987, to Van Tilburg disclose preferred sanitary napkins with flaps and are incorporated herein by reference to illustrate flapped sanitary napkin constructions.

It is also well known in the art to fold the flaps to overlay the main body of the pad during the manufacturing process. For example, U.S. Pat. No. 4,759,754 to Korpman an adhesive tab is used for maintaining the flaps in the desired disposition overlaying the backsheet during packaging. U.S. Pat. No. 4,701,178 issued Oct. 20, 1987, to Glaug et al. discloses a sanitary napkin having a single release strip which covers the centrally located adhesive of the backsheet and over which release strip the flaps are folded.

Alternative means for maintaining the flaps in a folded disposition prior to first use of the sanitary napkin by the wearer are shown for example, in U.S. Pat. No. 4,285,343 to McNair which discloses a sanitary napkin with flaps (side panels) that are folded over the upper surface of the central absorbent element for packaging and at the time of the first use by the wearer, the flaps are usually unfolded to facilitate installation of the sanitary napkin into the wearer's undergarment. Adhesive patches on a garment facing surface of the flaps are covered with individual strips of release paper. An alternative method of holding the flaps in place is to utilize the release strip paper present on the attachment adhesive located on the flaps. EP 0 347 319 B1 to Marsot and WO 88/04546 to Ternstrom disclose the use of a single release paper in the form of a bridging strip across the flap adhesive patches for maintaining the flaps in the folded disposition prior to the wearer's first use of the sanitary napkin. Two additional examples of this technique are shown in U.S. Pat. No. 5,800,654, to Davis et al. and U.S. Pat. No. 5,662,639 to Tanaka et al. In these methods the attachment adhesive on the flaps is applied in a conventional manner, i.e. via a transfer coating method and a single sheet of release paper acts both as a protective peel strip for the adhesively coated flaps and as a means to hold the flaps in their folded position.

Use of this method has several drawbacks. In particular, it requires that the flaps be maintained in a parallel position relative to one another. If one or both flaps becomes skewed during manufacture, the adhesive will not be correctly placed on one or both of the flaps, thus rendering it useless. One method of overcoming this problem is to make the peel strip quite large to accommodate this potential skewing.

SUMMARY OF THE INVENTION

Accordingly, it is an object of this invention to overcome certain problems of the prior art. Particularly, it is an object of this invention to provide a means to conveniently maintain the flaps in their manufactured, folded position and to do so as to minimize the effects of any skewing problems. Further, this method would accommodate designs in which asymmetrical flaps or uniquely sized releasable strips are employed, without using an excessively large amount of release paper.

In accordance with the present invention, there has been provided a novel a sanitary napkin comprising a liquid-permeable topsheet, a liquid-impermeable backsheet bonded to said topsheet, a liquid-absorbent core disposed between said topsheet and said backsheet, said napkin having transversely opposite side edges and first and second flaps each having upper and lower surfaces and extending outward from said transversely opposite side edges of said napkin and folded back onto said topsheet above said core respectively, wherein: each flap having a layer of adhesive on at least a portion of the lower surface of each said flap and a release strip covering each said layer of adhesive, each said release strip having a first and second surface, each said first surface having a release coating thereon and being in facing relationship with said adhesive layer and thereby creating an adhesive bond between said first surface and said flap; each said second surface having a layer of cohesive material on at least a portion thereof; and, a bridging strip having an outer and an inner surface, said inner surface being in a facing relationship with the second surface of each of said release strips, said inner surface having a layer of cohesive material on at least a portion thereof such that each said layer of cohesive material creates a cohesive bond between said bridging strip and each of said release strips.

Also provided in accordance with the present invention is a novel sanitary napkin comprising a liquid-permeable topsheet, a liquid-impermeable backsheet bonded to said topsheet, a liquid-absorbent core disposed between said topsheet and said backsheet, said napkin having transversely opposite side edges and first and second flaps each having upper and lower surfaces and extending outward from said transversely opposite side edges of said napkin and folded back onto said topsheet above said core respectively, wherein: each flap having a layer of adhesive on at least a portion of the lower surface of each said flap and a release strip covering each said layer of adhesive, each said release strip having a first and second surface, each said first surface having a release coating thereon and being in facing relationship with said adhesive layer and thereby creating an adhesive bond between said first surface and said flap; each said second surface having a layer of cohesive material on at least a portion thereof; and, a bridging strip having an outer and an inner surface, said inner surface being in a facing relationship with the second surface of each of said release strips; said bridging strip further having first and second end portions, the first end portion being folded back onto the inner surface of said bridging strip; each end portion that is in a facing position with the second surface of each of said release strips, having a layer of cohesive material on at least a portion thereof, such that each said layer of cohesive material creates a cohesive bond between said bridging strip and each of said release strips.

Still further provided in accordance with the present invention is a novel sanitary napkin comprising a liquid-permeable topsheet, a liquid-impermeable backsheet bonded to said topsheet, a liquid-absorbent core disposed between said topsheet and said backsheet, said napkin having a two transversely opposite side edges and two transversely opposite end edges, said napkin having a first pair of flaps located in a region of the napkin substantially equidistant between said end edges, said first pair of flaps adapted to be folded over a crotch portion of an undergarment; said napkin having a second pair of flaps located in a region of the napkin substantially adjacent to one of said two transversely opposite end edges, wherein: each flap of said first and second pair of flaps having an upper and a lower surface and each flap extending outward from said transversely opposite side edges of said napkin and folded back onto said topsheet above said core respectively, each flap having a layer of adhesive on at least a portion of the lower surface of each said flap and a release strip covering each said layer of adhesive, each said release strip having a first and second surface, each said first surface having a release coating thereon and being in facing relationship with said adhesive layer and thereby creating an adhesive bond between said first surface and said flap; each said second surface having a layer of cohesive material on at least a portion thereof; and, a bridging strip comprising an outer and an inner surface, said inner surface being in a facing relationship with the second surface of each of said release strips, said inner surface having a layer of cohesive material on at least a portion thereof such that each said layer of cohesive material creates a cohesive bond between said bridging strip and each of said release strips.

Still further provided with the present invention is a novel sanitary napkin comprising a liquid-permeable topsheet, a liquid-impermeable backsheet bonded to said topsheet, a liquid-absorbent core disposed between said topsheet and said backsheet, said napkin having a two transversely opposite side edges and two transversely opposite end edges, said napkin having a first pair of flaps located in a region of the napkin substantially equidistant between said end edges, said first pair of flaps adapted to be folded over a crotch portion of an undergarment; said napkin having a second pair of flaps located in a region of the napkin substantially adjacent to one of said two transversely opposite end edges, wherein: each flap of said first and second pair of flaps having an upper and a lower surface and each flap extending outward from said transversely opposite side edges of said napkin and folded back onto said topsheet above said core respectively, each flap having a layer of adhesive on at least a portion of the lower surface of each said flap and a release strip covering each said layer of adhesive, each said release strip having a first and second surface, each said first surface having a release coating thereon and being in facing relationship with said adhesive layer and thereby creating an adhesive bond between said first surface and said flap; each said second surface having a layer of cohesive material on at least a portion thereof; and, a first and second bridging strip, wherein each of said bridging strips comprise an outer and an inner surface, said inner surface being in a facing relationship with the second surface of each of said release strips, wherein said inner surface of the first bridging strip comprises a layer of cohesive material on at least a portion thereof thereby creating a cohesive bond between said first bridging strip and each of said release strips of said first pair of flaps, and wherein said inner surface of the second bridging strip comprises a layer of cohesive material on at least a portion thereof thereby creating a cohesive bond between said second bridging strip and each of said release strips of said second pair of flaps.

Still further provided with the present invention is a novel process for manufacturing sanitary napkins in which cohesive is used to join a bridging strip to a sanitary napkin having a liquid pervious topsheet, a liquid impervious backsheet at least partially peripherally joined to said topsheet, an absorbent core intermediate said topsheet and said backsheet, two transversely opposite side edges, and one or more flaps extending outwardly from each transversely opposite side edge, each of said flaps having a face generally coextensive of said topsheet and a face generally coextensive of said backsheet, said process comprising the steps of providing said sanitary napkin in a generally flat position; applying to a section of the face of each said flap coextensive of said backsheet generally contemporaneously an adhesive and a release strip with said adhesive in contacting relationship with said faces, said release strip comprising a side facing said adhesive and a side opposite said adhesive; folding each of said flaps about a line parallel to said transversely opposite side edge so that at least a portion of each of said flap faces that is generally coextensive of said topsheet contacts at least a portion of said topsheet that directly overlies said core, said folding pattern exposing each of said flap faces that is generally coextensive of said backsheet; applying to the side of each release strip opposite said adhesive a cohesive material; providing a bridging strip material having top and bottom surfaces, the bottom surface having a layer of said cohesive material on at least a portion thereof; cutting said bridging strip material to a predetermined length; and, placing said bridging strip material over each release strip thereby creating a cohesive bond between said bridging strip material and each said release strip.

DETAILED DESCRIPTION OF THE INVENTION

Further characteristics and advantages of the invention will become clear from the following detailed description, appended drawings, and non-limiting examples.

Figure 1:
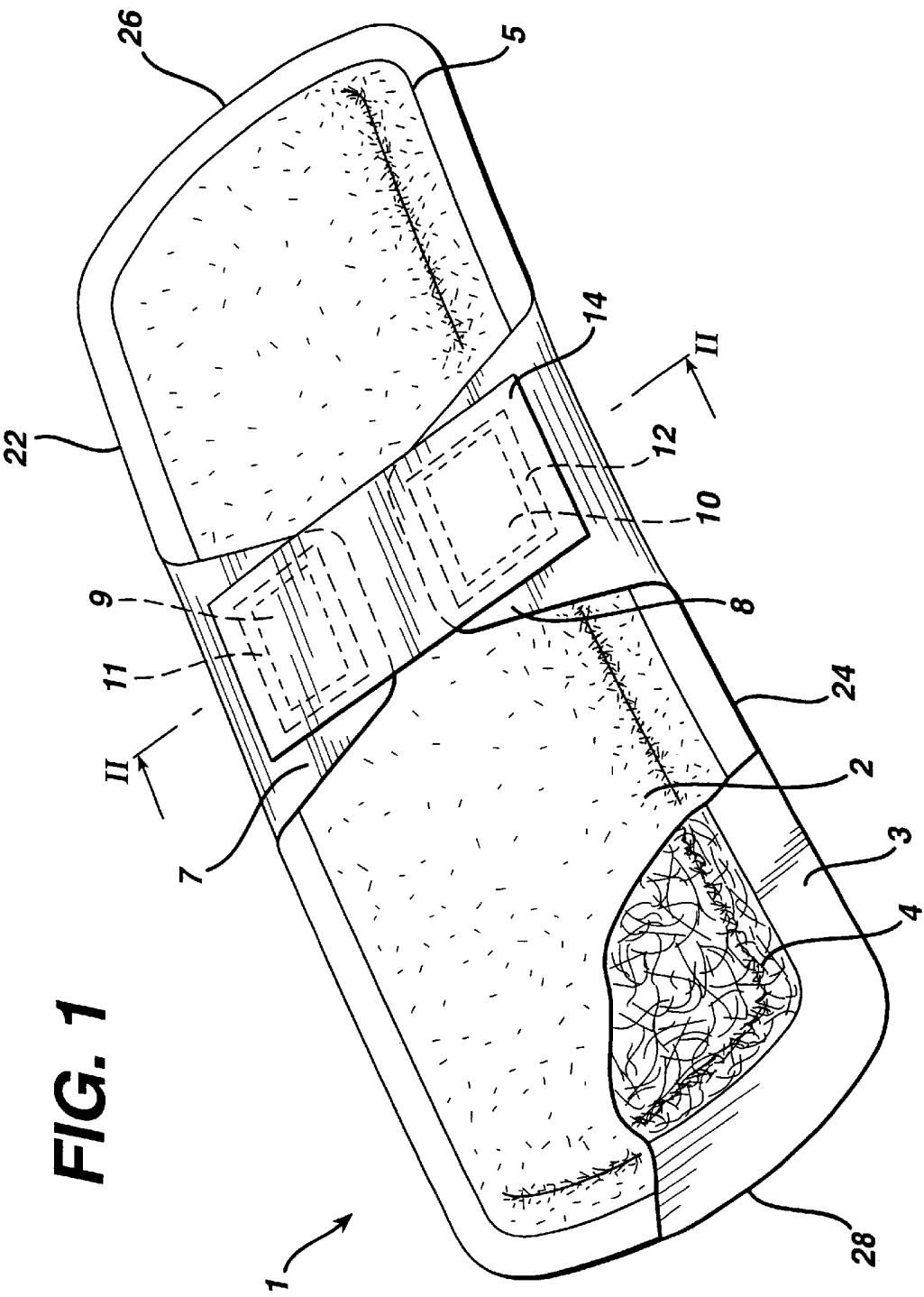
FIG. 1 is a perspective view showing a sanitary napkin of the preferred embodiment of the present invention as partially broken away.

As shown in FIG. 1, the invention comprises a disposable absorbent article, particularly a sanitary napkin 1. The sanitary napkin 1 is adapted to be worn in a user's undergarment and used to collect vaginal discharges, such as menses, and prevent soiling of the wearer's clothing by such discharges. The sanitary napkin 1 features a liquid pervious topsheet 2, a liquid impervious backsheet 3, an absorbent core 4 intermediate the topsheet 2 and the backsheet 3. The perimeter of the sanitary napkin 1 is defined by two transversely opposite side edges 22, 24 and two transversely opposite end edges 26, 28. In the preferred embodiment depicted in FIG. 1 two flaps 7, 8 extend from transversely opposite side edges 22, 24 and are adapted to be folded over a crotch portion of the user's undergarment, which flaps are folded back onto the topsheet 2 prior to use.

Associated with the sanitary napkin 1 is a means, such as adhesive, for releasably affixing the sanitary napkin 1 to the undergarment of a wearer. In particular, as depicted in FIG. 1, each flap 7,8 has an adhesive zone 9, 10, respectively. Preferentially, each such adhesive zone is associated with the face of the flap which contacts the undergarment of the wearer. Further, each such adhesive zone 9, 10 is covered by a release strip 11, 12, respectively.

The various embodiments of release strips 11, 12 described herein may be advantageously made of kraft paper, calendered paper, or any other materials well known in the art for such purpose. Preferably, the face of each release strip 11, 12 which contacts each adhesive zone 9,10 has a release coating, such as silicone, to easily facilitate removal of the release strip from the flaps. The opposite face of each release strip 11, 12, that is the side that is not in contact with the adhesive zone 9, 10 contains a layer of cohesive material on at least a portion of the release strip.

An important feature of the present invention, as depicted in FIG. 1, is a bridging strip 14 which contains a cohesive material on the side facing the release strips 11, 12. Accordingly, a cohesive bond is established between the bridging strip 14 and each of the release strips 11, 12. Use of this bridging strip 14 has several advantages over the prior art.

Use of the bridging strip 14 provides a means for maintaining the flaps 7,8 in the topsheet facing relationship of FIG. 1 during packaging and prior to first use by the wearer. As used herein the "first use by the wearer" refers to the initial installation of the sanitary napkin 1 into the undergarment. Moreover, this function is achieved by not requiring a single, enlarged release strip. Thus utilizing a bridging strip in this manner permits the use of a less expensive material than that of a larger release strip. Further, the use of such a bridging strip as a backing to the release strips allows a material to be used for the release strips.

Materials to be utilized for the bridging strip include but are not limited various films, foils, and papers that are well known in the art. In the preferred embodiment of the invention, a paper is used as the bridging strip material, said paper having a weight range of 10 to 90 lbs./ream (1 ream=3000 sq. ft.). This weight range is also applicable to the release strips of the present invention. In a more preferred embodiment of the present invention, the weight range is from about 19 to 50 lbs./ream for both the release strip and bridging strip materials. In the most preferred embodiment of the present invention, the weight range is 25 to 35 lbs./ream, thus reducing cost of these materials and reducing the thickness of the assembled napkin.

Figure 2:
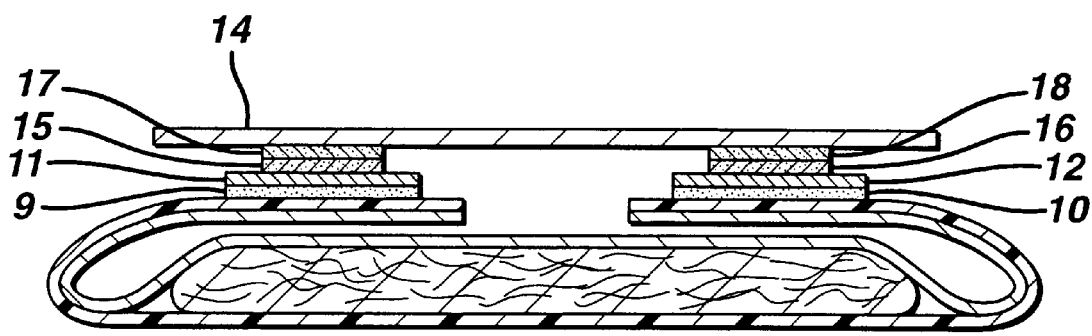
FIG. 2 is a sectional view taken along a line II—II in FIG. 1.

FIG. 2 depicts a cross-sectional view of the embodiment shown in FIG. 1 wherein the bridging strip 14 is shown to be positioned over the release strips 11, 12. Depicted in FIG. 2 is the cohesive layers 15, 16 applied to the face of each release strip 11, 12 that is not in contact with the adhesive zones 9, 10. Further depicted is the cohesive layers 17, 18 applied to sections of the bridging strip 14 to thereby create a cohesive bond between the bridging strip 14 and the release strips 11, 12.

Use of such cohesives are well known. Examples of water-based emulsions commonly used in the industry are: Natural Rubber Latex (cis 1–4 polyisoprene), polyurethane, acrylic, and polyvinyl acetate. In the preferred embodiment of the invention NP-4129 from HB Fuller Co. was utilized. An alternative embodiment employed VULTEX 3-S-740 from General Latex Co. as the cohesive. The range of coating weights used in these embodiments 0.5–2.1 lbs. of adhesive per ream of paper (i.e., 4.5–16.5 grams/ meter$^2$) per treated surface (e.g. cohesive layers 15, 16, 17 and 18). Still higher coating weights are permitted under alternative embodiments of the invention.

In the embodiment of the invention depicted in FIG. 2, the bridging strip is depicted as extending beyond the longitudinal edges of both release strips in an asymmetric manner. This is merely an illustrative example as the invention contemplates that the bridging strip can end in a symmetric manner with regard to the release strips, and can end contemporaneously with the longitudinal edges of the release strips. An further alternative embodiment of the invention has the bridging strip terminating prior to one or both of the longitudinal edges of the release strips.

Figure 3:
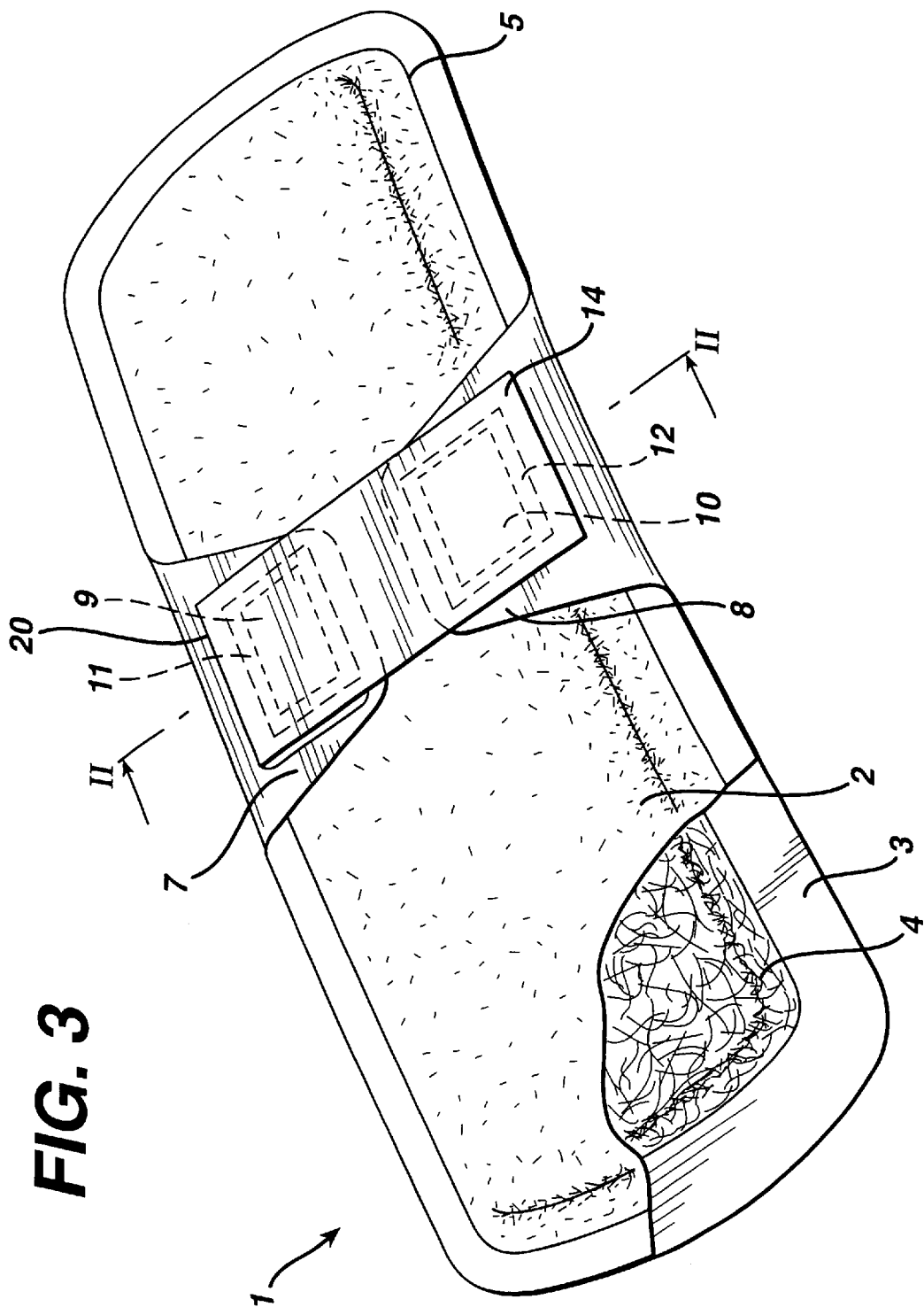
FIG. 3 a perspective view showing a sanitary napkin of a second preferred embodiment of the present invention as partially broken away.
Figure 4:
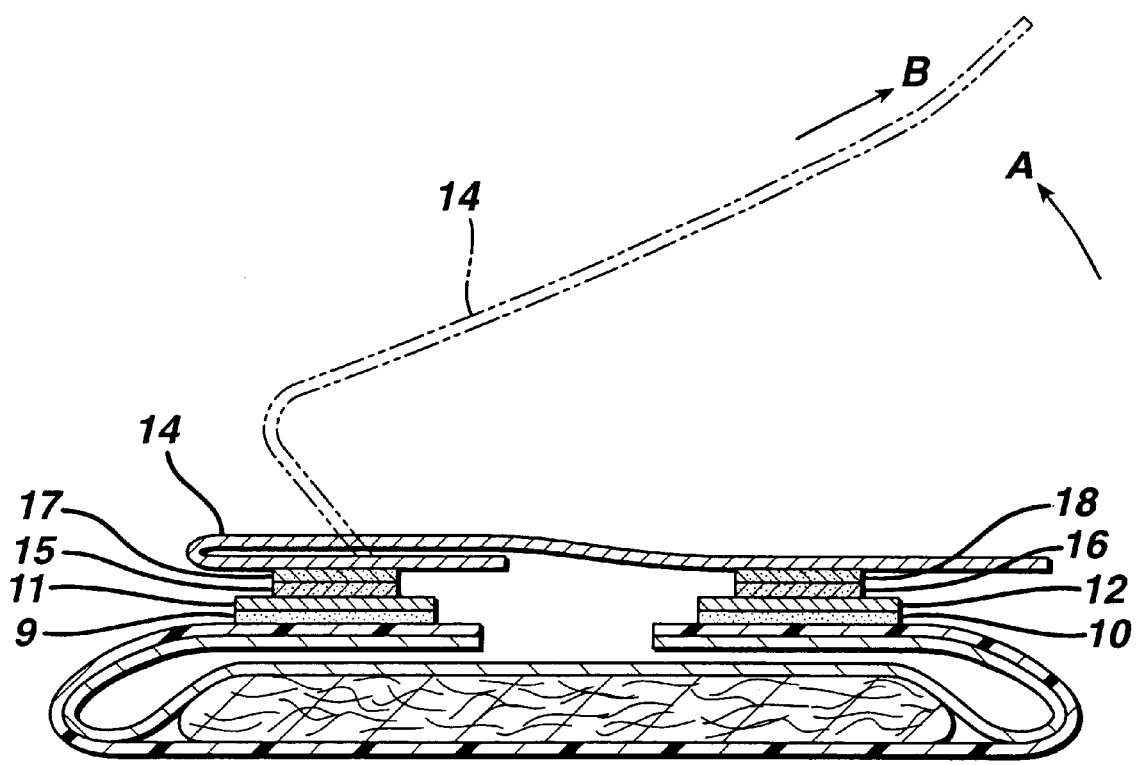
FIG. 4 is a sectional view taken along a line II—II in FIG. 3.

In embodiment depicted in FIG. 3 the portion of the bridging strip 14 above release strip 11 has been folded back along a fold line 20 prior to its attachment to the release strip 11. Thus as seen in FIG. 4, for the wearer to peel the bridging strip 14 off the flaps, the napkin 1 is held with a wearer's one hand and the bridging strip 14 is pulled up obliquely leftward in the direction as indicted by an arrow "A" to thereby peel the bridging strip 14 of the flaps as indicated by imaginary lines in FIG. 4. Then the bridging strip 14 is pulled up obliquely rightward in the direction as indicated by an arrow "B" to complete its removal. In this manner, the bridging strip 14 can be peeled off the flaps 7, 8 without shifting a wearer's hand from one end portion to the other end portion of the bridging strip.

In each of the embodiments depicted in FIGS. 1–4 above, establishing a cohesive bond between the bridging strip 14 and the release strips 11, 12 of greater strength than that of the adhesive bond between the release strips 11, 12 and their respective adhesive zones 9, 10 results in the removal of the bridging strip simultaneously removing the release strips. This has the advantages to the wearer of easier removal of these strips while reducing the number of individual items that need to be discarded.

Alternatively, by making the cohesive bond of lesser strength than the adhesive bonds, the bridging strip 14 still maintains its function of securing the flaps in their folded position yet permits subsequent, individual removal of the release strips. This has the advantage of having the adhesive area of only one flap exposed at a time, thus permitting the user to properly position this flap without having to be concerned about the second flap's exposed adhesive adhering to an undesirable location.

In yet another alternative embodiment, only one of the cohesive bonds would be stronger than the adhesive bond, while the second cohesive bond would be weaker. This embodiment would combine the benefits described above. That is, removal of the bridging strip would simultaneously remove only one release strip (associated with the flap having the cohesive bond stronger than the adhesive bond) thus facilitating removal of that release strip and minimizing the number of individual items that need to be discarded. Further, it permits the user to position and secure one flap prior to the adhesive on the second flap being exposed.

Figure 5:
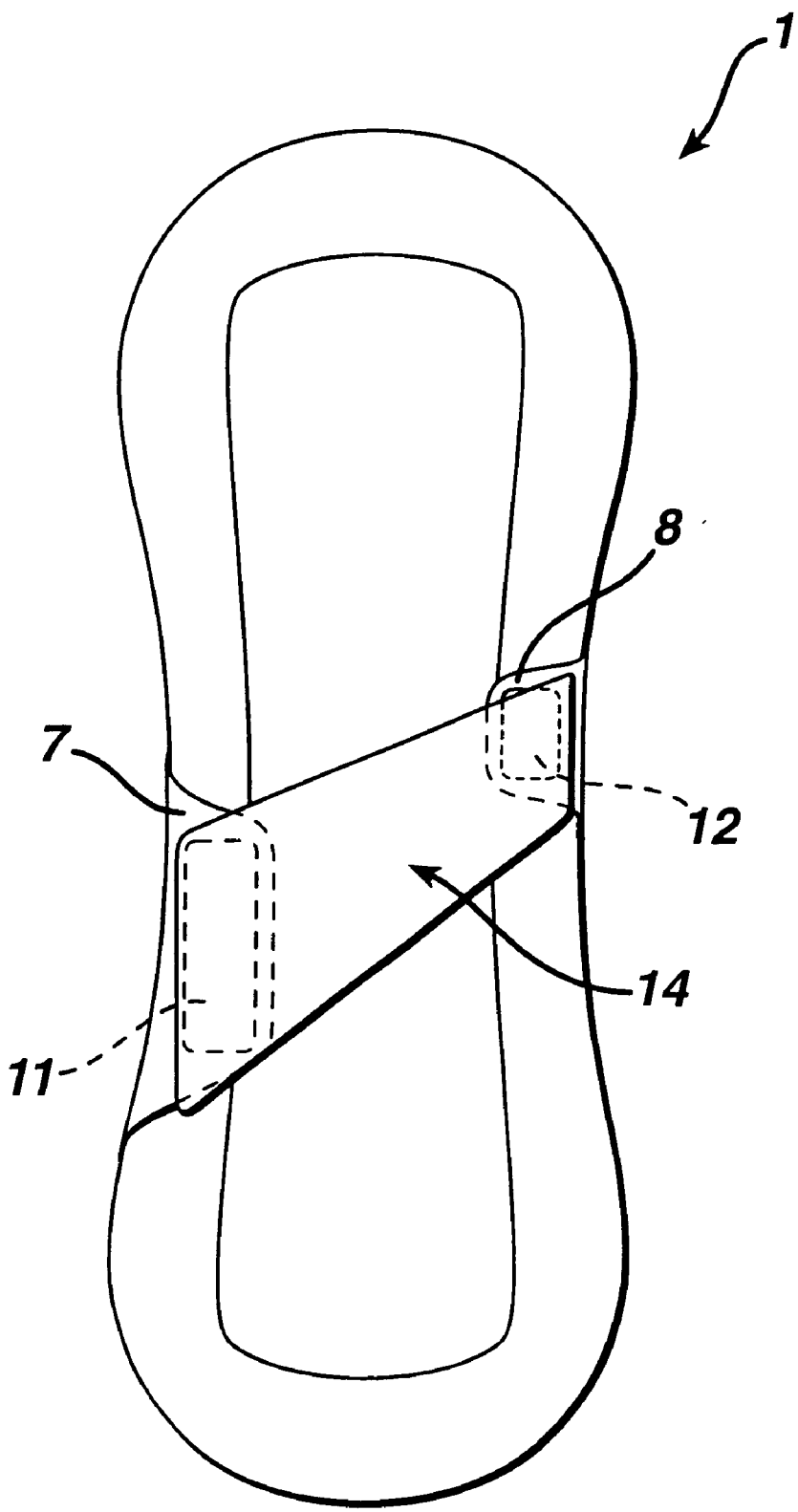
FIG. 5 is a perspective view showing a sanitary napkin of a third embodiment of the present invention.

In FIG. 5 depicts another embodiment of the present invention which illustrates the flexibility as to size and shape of the bridging. That is, in this embodiment the flaps 7, 8 of the sanitary napkin 1 vary in size and shape. Moreover, they are asymmetrical disposed. Use of a large release strip to hold the flaps in place, as taught in the prior art (e.g., U.S. Pat. No. 5,800,654, to Davis et al. and U.S. Pat. No. 5,662,639 to Tanaka et al.) requires that such a single release strip be correctly sized and positioned in order that the adhesive is properly placed on the flaps.

In the present invention each release strip need only be positioned with respect to its corresponding flap. The bridging strip is then positioned over a portion of each flap. Such positioning is less critical especially in light of the nature of the cohesive material itself. That is, should a portion of the cohesive layer applied to a flap not be covered by the bridging strip, the exposed cohesive will not result in an exposed sticky surface as the cohesive material will only adhere to itself. On the other hand, should the prior art release strip not cover a section of the adhesive zone on one or more flaps, an exposed adhesive surface results which causes numerous problems in manufacturing, packaging and use of the napkin. Further, use of a non-destructive, re-bondable cohesive in an alternative embodiment of the invention permits the bridging strip, once removed, to be reattached to one or more of the release strips.

Figure 6:
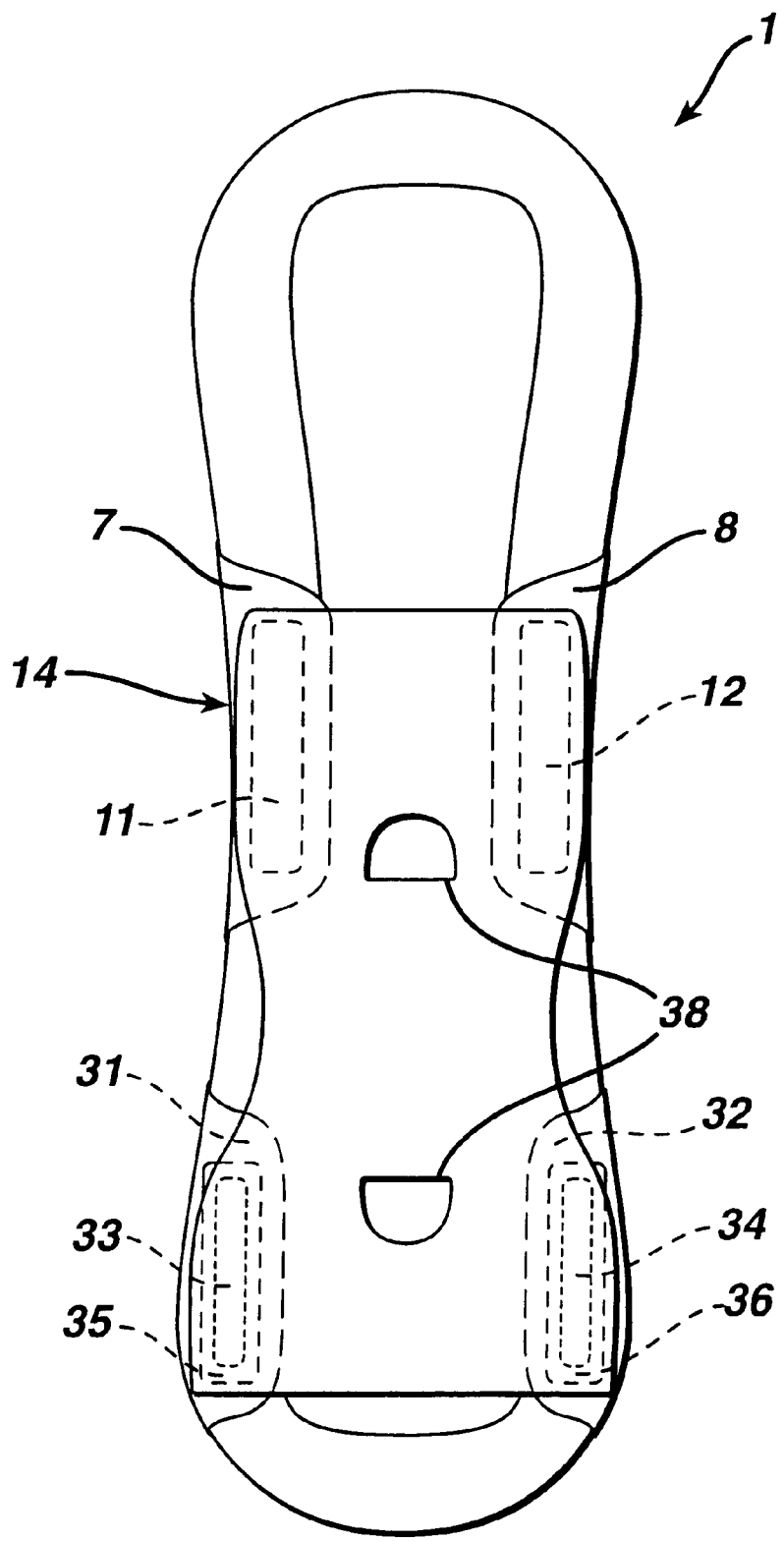
FIG. 6 is a perspective view showing a sanitary napkin of a fourth embodiment of the present invention.

FIG. 6 depicts an alternative embodiment of the invention wherein the sanitary napkin 1 comprises hip guards, an additional pair of flaps 31, 32 each having an adhesive zone, 33, 34. With four such flaps, positioning of a unitary release strip as taught by the prior art becomes even more difficult to perform effectively. The embodiment of the present invention, as depicted in FIG. 6 permits each flap's adhesive zone to be covered by a separate release strip, 35, 36. As depicted in previous embodiments above, the present invention uses cohesive layers to then form a cohesive bond between a bridging strip and the release strips. Such a bridging strip need not be specially treated paper such as the silicone coated unitary release strip of the prior art. In the embodiment illustrated in FIG. 6 finger lifts are depicted which would aid the user in the removal of the bridging strip. Alternatively, tabs could be located on the bridging strip at one or more locations (not shown).

Methods of making sanitary napkins having flaps are well known in the art. U.S. Pat. No. 5,800,654 to Davis et al. relates to such a method of manufacturing wherein the flaps are folded onto the topsheet of the napkin and secured by a unitary release strip. Davis is incorporated herein by reference to illustrate the basic, well-known methods of this manufacturing process.

The present invention differs from Davis in that the adhesive zone of each flap is covered by a separate release strip. This method of manufacture is also well known in the art. In the preferred embodiment of the invention, once the flaps are folded onto the topsheet, these individual release strips have a layer of cohesive material placed on at least a portion thereof. This same cohesive material has been placed onto one side of a bridging strip material. This bridging strip material is then cut to a sufficient size to cover each of the cohesively treated sides of the release strips and place over said strips. An alternative embodiment of the invention permits treating the release strips with cohesive prior to the folding operation. Another alternative embodiment of the present invention permits applying the cohesive material to the bridging strip material after it has been cut to size.

With each of these embodiments, once the bridging strip is brought into contact with the release strips, a pressure sufficient to form a cohesive bond is applied. This cohesive bond between the bridging strip and the release strips holds the flaps in their folded position for the balance of the sanitary napkin manufacturing and packaging process.

The specification and embodiments above are presented to aid in the complete and non-limiting understanding of the invention disclosed herein. Since many variations and embodiments of the invention can be made without departing from its spirit and scope, the invention resides in the claims hereinafter appended.

We claim:

1. A sanitary napkin comprising a liquid-permeable topsheet, a liquid-impermeable backsheet bonded to said topsheet, a liquid-absorbent core disposed between said topsheet and said backsheet, said napkin having transversely opposite side edges and first and second flaps each having upper and lower surfaces and extending outward from said transversely opposite side edges of said napkin and folded back onto said topsheet above said core respectively, wherein:

each flap having a layer of adhesive on at least a portion of the lower surface of each said flap and a release strip covering each said layer of adhesive, each said release strip having a first and second surface, each said first surface having a release coating thereon and being in facing relationship with said adhesive layer and thereby creating a releasable adhesive bond between said first surface and said flap;

each said second surface having a layer of cohesive material on at least a portion thereof; and, a bridging strip having an outer and an inner surface, said inner surface being in a facing relationship with the second surface of each of said release strips, said inner surface having a layer of cohesive material on at least a portion thereof such that each said layer of cohesive material creates a cohesive bond between said bridging strip and each of said release strips.

2. The sanitary napkin according to claim 1, wherein each said cohesive bond between said bridging strip and each of said release strips has a greater strength than each of said adhesive bonds, such that removal of the bridging strip by a user simultaneously removes each of said release strips from its respective flap.

3. The sanitary napkin according to claim 1, wherein at least one of said cohesive bonds between said bridging strip and said release strips has a lesser strength than said adhesive bond.

4. The sanitary napkin according to claim 1, wherein said bridging strip having a lengthwise dimension and a widthwise dimension, both dimensions being sufficiently large such that each said release strip is completely covered by said bridging strip.

5. The sanitary napkin according to claim 1, wherein said bridging strip having a lengthwise dimension and a widthwise dimension, at least one said dimension being insufficiently large such that at least one of said release strips is not completely covered by said bridging strip.

6. The sanitary napkin according to claim 1, wherein said bridging strip having a lengthwise dimension sufficiently large such that one or more portions of said bridging strip extend beyond at least one of said side edges of the napkin.

7. The sanitary napkin according to claim 1, wherein said bridging strip having a lengthwise dimension insufficiently large such no portion of said bridging strip extends beyond said side edges of the napkin.

8. The sanitary napkin according to claim 1, wherein each said bridging strip and said release strips comprise materials having a weight range of 10 to 90 lbs./ream.

9. The sanitary napkin according to claim 1, wherein each said layer of cohesive material applied to both said bridging strip and said release strips is applied at a minimum coating weight of 0.5 lbs. of adhesive per ream.

10. A sanitary napkin comprising a liquid-permeable topsheet, a liquid-impermeable backsheet bonded to said topsheet, a liquid-absorbent core disposed between said topsheet and said backsheet, said napkin having transversely opposite side edges and first and second flaps each having upper and lower surfaces and extending outward from said transversely opposite side edges of said napkin and folded back onto said topsheet above said core respectively, wherein:

each flap having a layer of adhesive on at least a portion of the lower surface of each said flap and a release strip covering each said layer of adhesive, each said release strip having a first and second surface, each said first surface having a release coating thereon and being in facing relationship with said adhesive layer and thereby creating a releasable adhesive bond between said first surface and said flap;

each said second surface having a layer of cohesive material on at least a portion thereof; and, a bridging strip having an outer and an inner surface, said inner surface being in a facing relationship with the second surface of each of said release strips; said bridging strip further having first and second end portions, the first end portion being folded back onto the inner surface of said bridging strip; each end portion that is in a facing position with the second surface of each of said release strips, having a layer of cohesive material on at least a portion thereof, such that each said layer of cohesive material creates a cohesive bond between said bridging strip and each of said release strips.

11. The sanitary napkin according to claim 10, wherein each said cohesive bond between said bridging strip and each of said release strips has a greater strength than each of said adhesive bonds, such that removal of the bridging strip by a user simultaneously removes each of said release strips from its respective flap.

12. A sanitary napkin comprising a liquid-permeable topsheet, a liquid-impermeable backsheet bonded to said topsheet, a liquid-absorbent core disposed between said topsheet and said backsheet, said napkin having two transversely opposite side edges and two transversely opposite end edges, said napkin having a first pair of flaps located in a region of the napkin substantially equidistant between said end edges, said first pair of flaps adapted to be folded over a crotch portion of an undergarment; said napkin having a second pair of flaps located in a region of the napkin substantially adjacent to one of said two transversely opposite end edges, wherein:

each flap of said first and second pair of flaps having an upper and a lower surface and each flap extending outward from said transversely opposite side edges of said napkin and folded back onto said topsheet above said core respectively, each flap having a layer of adhesive on at least a portion of the lower surface of each said flap and a release strip covering each said layer of adhesive, each said release strip having a first and second surface, each said first surface having a release coating thereon and being in facing relationship with said adhesive layer and thereby creating a releasable adhesive bond between said first surface and said flap;

each said second surface having a layer of cohesive material on at least a portion thereof; and, a bridging strip comprising an outer and an inner surface, said inner surface being in a facing relationship with the second surface of each of said release strips, said inner surface having a layer of cohesive material on at least a portion thereof such that each said layer of cohesive material creates a cohesive bond between said bridging strip and each of said release strips.

13. The sanitary napkin according to claim 12, wherein each said cohesive bond between said bridging strip and each of said release strips has a greater strength than each of said adhesive bonds, such that removal of the ridging strip by a user simultaneously removes all of said release strips.

14. The sanitary napkin according to claim 12, wherein at least one of said cohesive bonds between said bridging strip and said release strips has a lesser strength than said adhesive bond.

15. The sanitary napkin according to claim 12, wherein said bridging strip having a lengthwise dimension and a widthwise dimension, both dimensions being sufficiently large such that each said release strip is completely covered by said bridging strip.

16. The sanitary napkin according to claim 12, wherein said bridging strip having a lengthwise dimension and a widthwise dimension, at least one said dimension being insufficiently large such that at least one of said release strips is not completely covered by said bridging strip.

17. The sanitary napkin according to claim 12, wherein said bridging strip having a lengthwise dimension sufficiently large such that one or more portions of said bridging strip extend beyond at least one of said side edges of the napkin.

18. The sanitary napkin according to claim 12, wherein said bridging strip having a lengthwise dimension insufficiently large such no portion of said bridging strip extends beyond said side edges of the napkin.

19. The sanitary napkin according to claim 12, wherein each said bridging strip and said release strips comprise materials having a weight range of 10 to 90 lbs./ream.

20. The sanitary napkin according to claim 12, wherein each said layer of cohesive material applied to both said bridging strip and said release strips is applied at a minimum coating weight of 0.5 lbs. of adhesive per ream.

21. A sanitary napkin comprising a liquid-permeable topsheet, a liquid-impermeable backsheet bonded to said topsheet, a liquid-absorbent core disposed between said topsheet and said backsheet, said napkin having a two transversely opposite side edges and two transversely opposite end edges, said napkin having a first pair of flaps located in a region of the napkin substantially equidistant between said end edges, said first pair of flaps adapted to be folded over a crotch portion of an undergarment; said napkin having a second pair of flaps located in a region of the napkin substantially adjacent to one of said two transversely opposite end edges, wherein:

each flap of said first and second pair of flaps having an upper and a lower surface and each flap extending outward from said transversely opposite side edges of said napkin and folded back onto said topsheet above said core respectively, each flap having a layer of adhesive on at least a portion of the lower surface of each said flap and a release strip covering each said layer of adhesive, each said release strip having a first and second surface, each said first surface having a release coating thereon and being in facing relationship with said adhesive layer and thereby creating a releasable adhesive bond between said first surface and said flap;

each said second surface having a layer of cohesive material on at least a portion thereof; and, a first and second bridging strip, wherein each of said bridging strips comprise an outer and an inner surface, said inner surface being in a facing relationship with the second surface of each of said release strips, wherein said inner surface of the first bridging strip comprises a layer of cohesive material on at least a portion thereof thereby creating a cohesive bond between said first bridging strip and each of said release strips of said first pair of flaps, and wherein said inner surface of the second bridging strip comprises a layer of cohesive material on at least a portion thereof thereby creating a cohesive bond between said second bridging strip and each of said release strips of said second pair of flaps.

22. The sanitary napkin according to claim 21 wherein each said cohesive bond between said first bridging strip and each of said release strips of said first pair of flaps has a greater strength that each of said adhesive bonds of the first pair of flaps, such that removal of the first bridging strip by a user simultaneously removes each of said release strips from its respective flap of said first pair of flaps; and wherein each said cohesive bond between said second bridging strip and each of said release strips of said second pair of flaps has a greater strength that each of said adhesive bonds of the second pair of flaps, such that removal of the second bridging strip by a user simultaneously removes each of said release strips from its respective flap of said second pair of flaps.

23. A method for folding a sanitary napkin having flaps and maintaining said flaps in their folded configuration prior to use, wherein said sanitary napkin comprises a liquid pervious topsheet, a liquid impervious backsheet at least partially peripherally joined to said topsheet, an absorbent core intermediate said topsheet and said backsheet, two transversely opposite side edges, and one or more flaps extending outwardly from each transversely opposite side edge, each of said flaps having a face generally coextensive of said topsheet and a face generally coextensive of said backsheet, said method comprising the steps of:

providing said sanitary napkin in a generally flat position;

applying to a section of the face of each said flap coextensive of said backsheet generally contemporaneously an adhesive and a release strip with said adhesive in contacting relationship with said faces, said release strip comprising a side facing said adhesive and a side opposite said adhesive to which a layer of cohesive material has been applied to at least a portion thereof;

folding each of said flaps about a line parallel to said transversely opposite side edge so that at least a portion of each of said flap faces that is generally coextensive of said topsheet contacts at least a portion of said topsheet that directly overlies said core, said folding pattern exposing each of said flap faces that is generally coextensive of said backsheet;

providing a bridging strip material having top and bottom surfaces, the bottom surface having a layer of said cohesive material on at least a portion thereof;

cutting said bridging strip material to a predetermined length; and, placing said bridging strip material over each release strip thereby creating a cohesive bond between said bridging strip material and each said release strip.

24. The method of claim 23 wherein said step of applying cohesive to the release strip precedes said folding step.

* * * * *

UNITED STATES PATENT AND TRADEMARK OFFICE
CERTIFICATE OF CORRECTION

PATENT NO. : 6,447,495 B1
DATED : September 10, 2002
INVENTOR(S) : Joseph Luizzi and Melinda Cettina It is certified that error appears in the above-identified patent and that said Letters Patent is hereby corrected as shown below:

<u>Column 9,</u>
Line 66, "ridging" should be -- bridging --

Signed and Sealed this

Fifteenth Day of July, 2003

JAMES E. ROGAN
*Director of the United States Patent and Trademark Office*